United States Patent
Grass

(10) Patent No.: US 9,851,317 B2
(45) Date of Patent: Dec. 26, 2017

(54) DEVICE FOR ASCERTAINING A MEASURE OF A CALORIC VALUE OF A GAS

(71) Applicant: CONTINENTAL AUTOMOTIVE GMBH, Hannover (DE)

(72) Inventor: Phillippe Grass, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 261 days.

(21) Appl. No.: 14/768,728

(22) PCT Filed: Feb. 17, 2014

(86) PCT No.: PCT/EP2014/053006
§ 371 (c)(1),
(2) Date: Aug. 18, 2015

(87) PCT Pub. No.: WO2014/128077
PCT Pub. Date: Aug. 28, 2014

(65) Prior Publication Data
US 2015/0377807 A1    Dec. 31, 2015

(30) Foreign Application Priority Data
Feb. 19, 2013 (DE) .................... 10 2013 202 681

(51) Int. Cl.
*G01N 25/22* (2006.01)
*G01N 27/407* (2006.01)
(Continued)

(52) U.S. Cl.
CPC ......... *G01N 25/22* (2013.01); *G01N 27/4065* (2013.01); *G01N 33/225* (2013.01)

(58) Field of Classification Search
None
See application file for complete search history.

(56) References Cited

U.S. PATENT DOCUMENTS

| 4,158,166 A * | 6/1979 | Isenberg ............... F23N 5/006 |
| | | 204/426 |
| 4,231,733 A * | 11/1980 | Hickam ............... F23N 5/006 |
| | | 123/438 |

(Continued)

FOREIGN PATENT DOCUMENTS

| DE | 29 715 633 | 11/1997 |
| DE | 694 21 319 | 7/2000 |

(Continued)

*Primary Examiner* — Clayton E Laballe
*Assistant Examiner* — Leon W Rhodes, Jr.
(74) *Attorney, Agent, or Firm* — Cozen O'Connor

(57) ABSTRACT

A device for ascertaining a measure of a calorific value of a gas, having a membrane arranged between a first and a second electrode a controllable voltage/current source for generating a control voltage/current between the first and second electrode, and an analyzing device for ascertaining the measure of the calorific value of the gas. By applying the control voltage/current to the first and second electrode, oxygen is transported from an oxygen-containing reference gas into the gas through the membrane and is combusted with combustible components of the gas. The analyzing device ascertains the measure of the calorific value of the gas dependent on the generated control voltage/current a temperature of the membrane, or dependent on an impedance of the membrane.

15 Claims, 4 Drawing Sheets

(51) Int. Cl.
*G01N 33/22* (2006.01)
*G01N 27/406* (2006.01)

(56) References Cited

U.S. PATENT DOCUMENTS 4,285,790 A * 8/1981 Isenberg ............ G01N 27/4073
  204/400
5,080,765 A * 1/1992 Wang ................. G01N 27/4065
  204/425

FOREIGN PATENT DOCUMENTS

| DE | 101 29 065 | 12/2002 |
| EP | 0 438 859 | 7/1991 |
| GB | 2 099 589 | 12/1982 |

* cited by examiner

DEVICE FOR ASCERTAINING A MEASURE OF A CALORIC VALUE OF A GAS

CROSS REFERENCE TO RELATED APPLICATIONS

This is a U.S. national stage of application No. PCT/EP2014/053006, filed on Feb. 17, 2014. Priority is claimed on German Application No.: DE102013202681.1, filed Feb. 19, 2013, the content of which is incorporated herein by reference.

BACKGROUND OF THE INVENTION

1. Field of the Invention

The invention relates to a device for ascertaining a measure of a calorific value of a gas and a method for ascertaining a measure of a calorific value of a gas.

2. Detailed Description of Prior Art

Spark ignition engines operated with petrol or diesel as the fuel can be converted to operate with compressed natural gas (CNG). The gas usually has different components in different countries. In particular, the proportion of nitrogen or carbon dioxide reduces the calorific value of the gas. For correct regulation of the engine it is advantageous to know the calorific value of the gas.

SUMMARY OF THE INVENTION

It is desirable to specify a device for ascertaining a measure of a calorific value of a gas and a method for ascertaining a measure of a calorific value of a gas is to be specified.

One embodiment of a device for ascertaining a measure of a calorific value of a gas comprises a diaphragm designed to transport oxygen above a threshold value of a temperature, a heating apparatus for heating the diaphragm, a first electrode arranged on a first side of the diaphragm, and a second electrode arranged on a second side of the diaphragm, which is different than the first side. Furthermore, the device comprises a controllable voltage and/or a current source for generating a control voltage and/or a control current between the first and second electrodes for controlling the transporting of the oxygen through the diaphragm and an evaluation apparatus for ascertaining the measure of the calorific value of the gas, which has combustible gas portions. The controllable voltage/current source is designed to generate the control voltage/control current such that a quantity of oxygen is transported through the diaphragm as a function of a level of the control voltage/control current that the combustible portions of the gas burn if the first electrode is arranged in a first environment that contains the gas and the second electrode is arranged in a second environment that contains a reference gas, which is different from the gas, with the oxygen. The evaluation apparatus is designed to ascertain the measure of the calorific value of the gas as a function of the generated control voltage/generated control current or as a function of a level of the temperature of the diaphragm or as a function of an impedance of the diaphragm.

One embodiment of a method for ascertaining a measure of a calorific value of a gas comprises:

providing a device for ascertaining a calorific value of a gas as disclosed above, arranging the device such that the first electrode is arranged in a first environment and the second electrode is arranged in a second environment, applying a control voltage/control current between the first and second electrodes with a level such that a quantity of oxygen is transported from the second environment through the diaphragm to the first environment such that the combustible portions of the gas burn, burning the oxygen in the first environment of the first electrode, ascertaining the measure of the calorific value of the gas by evaluating a level of the control voltage/control current or by evaluating a level of the temperature of the diaphragm, or by evaluating an impedance between the first and second electrodes during the combustion process.

The diaphragm, the heating apparatus, and the first and second electrodes may be, for example, part of a lambda probe. A lambda probe is usually used to measure the residual oxygen content present in a combustion gas, to regulate the ratio of the combustion air to the fuel for the further combustion, with the result that neither an excess of fuel nor an excess of air occurs. The lambda probe can for this purpose be arranged between an environment with oxygen-containing reference air and an environment in which the exhaust gas stream is conducted.

An yttrium-doped (YSZ) ceramic can be used as a diaphragm between the first and second electrodes. So that the YSZ diaphragm reaches its oxygen ion-conducting capability in a lambda probe or so that oxygen ions can be pumped from one of the electrodes to the other electrode through the diaphragm, the diaphragm can be heated to approximately 700° C. by a heating apparatus. The lambda probe can contain a reference channel through which the oxygen-containing ambient air diffuses into the heated region of the sensor. When a lambda probe is used in a vehicle, the first electrode is arranged in the exhaust gas stream and the second electrode is arranged in a reference channel.

As a result of the difference in oxygen concentration between the exhaust gas stream and the oxygen-containing ambient air, ion diffusion of the oxygen occurs in a lambda probe, with the result that oxygen ions migrate from the high concentration of the reference air, and therefore from the second electrode, through the diaphragm to the first electrode or to the low oxygen concentration of the exhaust gas. The electrons which are necessary to ionize the oxygen atoms are supplied by the electrically conductive first and second electrodes. As a result, an electrical voltage can be tapped between the first and second electrodes. Based on this probe voltage it is possible to make a statement as to whether a large or small amount of oxygen is present in the exhaust gas stream.

According to one embodiment of the invention, using the device for ascertaining a measure of a calorific value of a gas the function of the lambda probe is converted to a MEMS oven. The oxygen required for the micro-combustion in the gas diffuses via the reference channel to the second electrode that is then operated as a pump cathode with a poling which is reversed compared to a customary lambda probe. In order to pump the oxygen from the reference gas into the gas whose calorific value is to be determined, the control voltage/control current is applied between the first and second electrode. As a result, oxygen ions are transported from the second electrode through the diaphragm to the first electrode located in the gas stream of the gas whose calorific value is to be ascertained.

The oxygen ions or the oxygen ions that are converted into molecular oxygen burn with the combustible portions of the gas in the region of the first electrode. The combustion process proceeds based on the catalytic action of the first and second electrodes which can be embodied, for example, as porous platinum electrodes, without the development of flames.

According to a first embodiment of the device or of the method for ascertaining a measure of the calorific value of a gas, the control voltage/control current generated by the controllable voltage/current source and is necessary to pump oxygen ions into the gas and to burn there with the gas, is evaluated by the evaluation apparatus. The control voltage/control current is generated by the controllable voltage/current source between the first and second electrodes, in successive time cycles only during the second duration based on, in each case, a first duration and a second duration which follows the latter. During the first duration, the voltage that occurs between the first and second electrodes is measured by a voltage-measuring apparatus. The control apparatus regulates the control voltage/control current as a function of the voltage that is measured during the first duration. For example, the control voltage/control current can be set in such a way that the voltage measured between the first and second electrodes has a level of approximately 450 mV.

According to one embodiment of the device or of the method for ascertaining a measure of the calorific value of the gas, in the case of the use of a controllable voltage source a voltage of approximately 0.3 V to 2 V is generated between the first and second electrodes by the controllable voltage source to pump oxygen ions from the reference gas into the gas whose calorific value is to be ascertained, and to burn them together with the combustible portions of the gas. The exothermic reaction brings about an increase in temperature of the diaphragm, which can be used as a measure of the calorific value.

According to one embodiment of the device or of the method, the heating apparatus can be embodied as a pulse-width-modulated heater. The pulse-width-modulated heater can be embodied such that the pulse-width modulation rate (PWM rate) of the heater rises automatically if the temperature of the diaphragm is too low for transporting oxygen ions, or drops automatically if the temperature of the diaphragm is too high or significantly above the threshold value of the temperature specified above. The increase in temperature of the diaphragm can be detected by evaluating the PWM rate of the heating apparatus, which drops due to the heating of the diaphragm as a result of the combustion process.

According to one embodiment of the device or of the method, an impedance between the first and second electrodes is ascertained by the evaluation apparatus in the pump pauses during the first duration of the successive time cycles.

In this context use is also made of the fact that the impedance of the diaphragm is temperature-dependent.

BRIEF DESCRIPTION OF THE DRAWINGS

The invention will be explained in more detail below with reference to figures which show exemplary embodiments of the present invention, of which.

DETAILED DESCRIPTION OF THE PRESENTLY PREFERRED EMBODIMENTS

Figure 1:
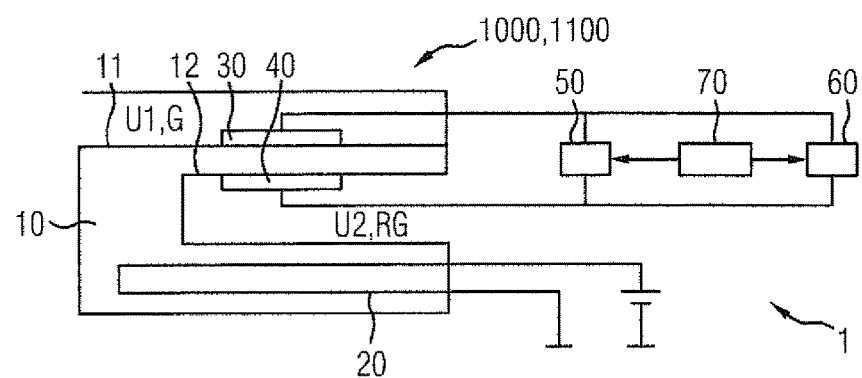
FIG. 1 is a device for ascertaining a measure of a calorific value of a gas.

FIGS. 1 to 7 show embodiments of a device for ascertaining a measure of a calorific value of a gas G that has combustible portions. In all the embodiments, the device has a diaphragm 10, a heating apparatus 20, a first electrode 30, a second electrode 40, a controllable voltage/current source 50, an evaluation apparatus 60 and a control apparatus 70 for controlling the controllable voltage/current source 50. Firstly, the common components of the different embodiments of the device for ascertaining a measure of the calorific value of a gas are specified. Details on the particular features of the respective embodiments are given subsequently.

In FIGS. 1 to 7 the device for ascertaining a calorific value of a gas, the diaphragm 10 can comprise, for example, a material made of an yttrium-doped ceramic. The diaphragm 10 can be embodied in such a way that it is suitable for transporting oxygen, in particular oxygen ions, in the case of heating above a threshold value of a temperature. The heating apparatus 20 can be designed to heat the diaphragm, in particular to heat the diaphragm to the threshold value of the temperature at which the diaphragm is permeable to oxygen. The first and second electrodes 30, 40 can be configured in a porous fashion from a material made of platinum. The first electrode 30 can be arranged on a first side 11 of the diaphragm 10, which is arranged in a first environment U1 of the gas G for whose calorific value a measure is to be determined. The second electrode 40 can be arranged on a second side 12 of the diaphragm 10, which is different from the first side. The second electrode 40 and therefore the second side 12 of the diaphragm 10 can be arranged in a second environment U2, which contains an oxygen-containing reference gas RG, which is different from the gas G.

The controllable voltage/current source 50 is designed to generate a control voltage/control current between the first and second electrodes 30, 40 for controlling the transporting of the oxygen through the diaphragm 10. The controllable voltage/current source 50 is designed to generate the control voltage/control current such that such a quantity of oxygen is transported through the diaphragm 10 as a function of a level of the control voltage/control current that the combustible portions of the gas G burn if the first electrode 30 is arranged in the first environment U1 comprising the gas G, and the second electrode 40 is arranged in the second environment U2 comprising the reference gas RG with the oxygen.

The control apparatus 70 actuates the controllable voltage/current source 50 in successive time cycles such that during a first duration of each of the time cycles no control voltage/no control current is generated by the controllable voltage/current source 50, and during a second duration of each of the time cycles, which follows the first duration, the control voltage/control current is generated with a level. The level of the control voltage/control current is selected such that sufficient oxygen is transported by the reference gas RG through the diaphragm to the first electrode 30 and burnt in the environment U1 together with the combustible components of the gas G if the first electrode 30 is arranged in the environment U1 of the gas, and the second electrode 40 is arranged in the environment U2 of the oxygen-containing reference gas RG.

The evaluation apparatus 60 ascertains the measure of the calorific value of the gas G. According to the embodiments shown in FIGS. 1 and 2 of the device for ascertaining the measure of the calorific value of the gas, the evaluation apparatus 60 ascertains the measure of the calorific value of the gas G as a function of the generated control voltage or the generated control current. According to the embodiments shown in FIGS. 3 and 4 of the device for ascertaining the measure of the calorific value of the gas, the evaluation apparatus 60 ascertains the measure of the calorific values of the gas G as a function of a level of the temperature of the diaphragm 10. In the embodiments shown in FIGS. 5, 6 and 7 of the device for ascertaining the measure of the calorific value of the gas the evaluation apparatus 60 that ascertains the measure of the calorific value of the gas G as a function of an impedance of the diaphragm 10.

The first electrode 30 is arranged in the environment U1 of the gas G for whose calorific value a measure is to be ascertained with the device. The second electrode 40 is arranged in the environment U2, which contains the oxygen-containing reference gas RG. The diaphragm 10 can be configured in such a way that the device has, around the second electrode 40, a channel RK with an inlet opening ERK for feeding the reference gas RG into the channel and thus to the second electrode 40. The channel RK is shaped such that the reference gas RG is fed to the second electrode 40 via the channel RK. At the inlet opening ERK of the channel RK, a diffusion barrier 130 can be provided via which the reference gas RG is fed into the channel RK and therefore passes to the second electrode 40.

In all of the embodiments of the device for ascertaining the calorific value of a gas, the arrangement comprised of the diaphragm 10, the heating apparatus 20 and the first and second electrodes 30, 40 can be part of a lambda probe 1000. In embodiments 1, 3 and 5, the diaphragm 10, the heating apparatus 20 and the first and second electrodes 30, 40 are configured as part of a bistable probe 1100.

In embodiments 2, 4, 6 and 7 the diaphragm 10, the heating apparatus 20 and the first and second electrodes 30, 40 are configured as part of a broadband probe 1200. The broadband probe 1100 comprises a Nernst cell 1210 and a pump cell 1220. The Nernst cell 1210 comprises the diaphragm 10 and the first and second electrodes 30, 40. The pump cell 1200 can have a third electrode 110 and a fourth electrode 120. The diaphragm is shaped between the Nernst cell 1210 and the pump cell 1220 such that a channel MG with an inlet opening EMG for feeding the gas G into the channel MG is formed.

A diffusion barrier 140 through which the gas G is fed into the channel MK can be arranged at the inlet opening EMG.

Since the channel MK is connected to the diaphragm-side end and since the diffusion barrier 40 is provided at the inlet opening EMG, the channel MK in embodiments 2, 4, 6 and 7 forms a measuring chamber into which the oxygen is pumped via the Nernst cell 1210. The combustion process of the oxygen and of the combustible components of the gas G proceeds at the first electrode 30 within the measuring chamber MK. As a result of the provision of the diffusion barrier 130 at the inlet opening ERK of the channel RK it can be ensured that in the event of a rupture of the diaphragm 10 no oxygen can penetrate the measuring chamber MK in an uncontrolled fashion from the oxygen-containing environment of the reference gas.

Figure 2:
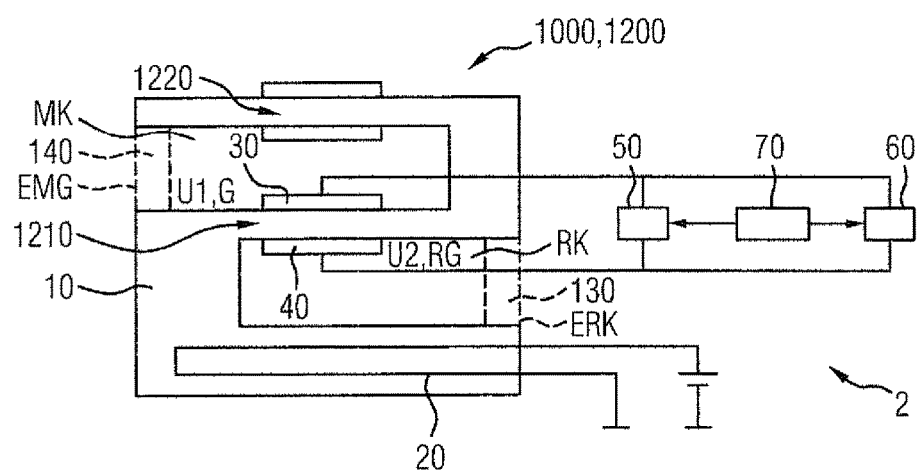
FIG. 2 is a device for ascertaining a measure of a calorific value of a gas.

In the devices shown in FIGS. 1 and 2, the controllable voltage/current source 50 is connected to the first and second electrodes 30, 40 to apply the control voltage/control current between the first and second electrodes 30, 40. Furthermore, the device 1 and 2 has a voltage-measuring apparatus 80, which is also connected to the first and second electrodes 30, 40. The voltage-measuring apparatus 80 is designed to ascertain the voltage level, applied between the first and second electrodes 30, 40, during the first duration of each of the time cycles. In the embodiments 1 and 2 of the device, the control apparatus 70 is designed to actuate the controllable voltage/current source 50 such that the controllable voltage/current source 50 generates the level of the control voltage/control current during the second duration of each of the time cycles as a function of the voltage level ascertained during the first duration of each of the time cycles.

FIGS. 1 and 2 of the device for ascertaining the measure of a calorific value of a gas differ in that in FIG. 1 the diaphragm 10, the heating apparatus 20, and the first and second electrodes 30, 40 are part of a bistable probe, while in FIG. 2 the diaphragm 10, the heating apparatus 20, and the first and second electrodes 30, 40 are part of a linear lambda probe or broadband probe. In FIG. 2, the pump cell 1220 can remain unconnected.

To ascertain a measure of a calorific value of the gas G by the device according to embodiments 1 and 2, the device is arranged such that the first electrode 30 is in contact with the gas G, and the oxygen-containing reference gas RG flows around the second electrode 40. The control apparatus 70 actuates the controllable voltage/current source 50 such that a control voltage/control current is applied between the first and second electrodes 30, 40 with a level such that such a quantity of oxygen is transported from the second environment U2 through the diaphragm 10 to the first environment U1 such that the oxygen in the region around the first electrode 30 burns together with the combustible components of the gas G.

During the first duration of each of the time cycles of the measurement, no control voltage/control current is applied between the first and second electrodes 30, 40 from the controllable voltage/current source 50. Instead, during the first duration the voltage level between the first and second electrodes 30, 40 is measured by the voltage-measuring apparatus 80. During the second duration of each of the time cycles, which follows the first duration, of the measurement, the control apparatus 70 actuates the controllable voltage/current source 50 in such a way that the control voltage/control current is generated as a function of the voltage level, which was previously measured between the first and second electrodes 30, 40. The level of the control voltage/control current can be generated, for example during each second duration of the measuring time cycles, such that the voltage level measured during the first duration of the measuring time cycles, between the first and second electrodes 30, 40, assumes a voltage level of approximately 450 mV. The level of the control voltage, which is regulated in this way or of the control current regulated in this way is evaluated by the evaluation apparatus 60, and is a measure of the calorific value of the gas G.

Figure 3:
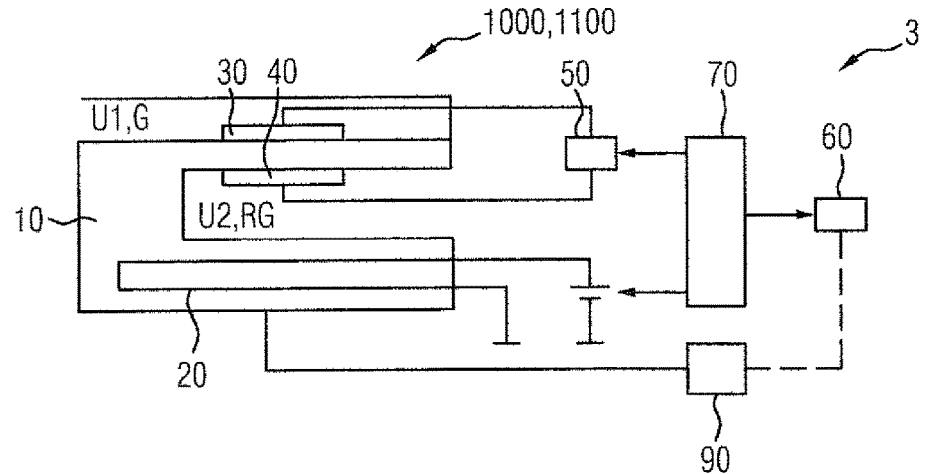
FIG. 3 is a device for ascertaining a measure of a calorific value of a gas.
Figure 4:
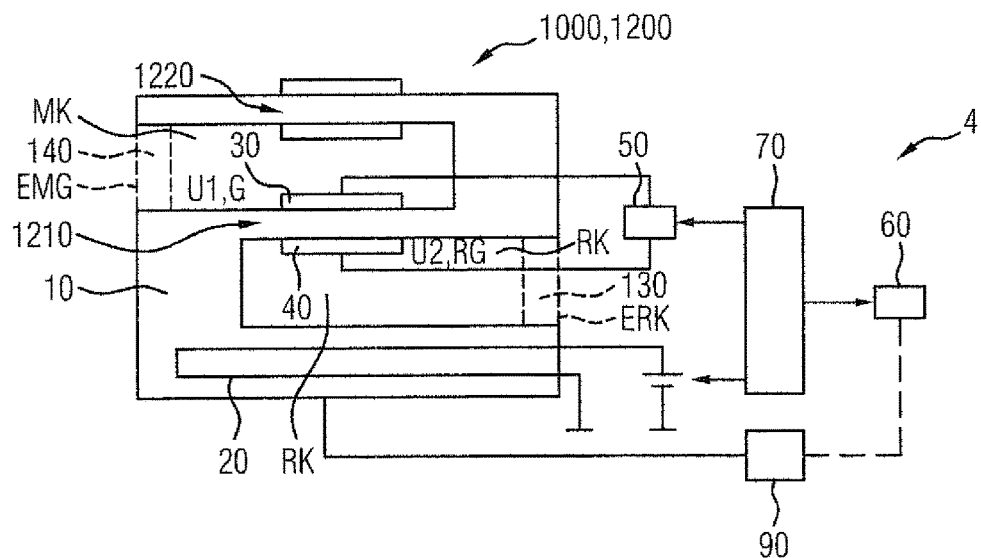
FIG. 4 is a device for ascertaining a measure of a calorific value of a gas.

In the devices shown in FIGS. 3 and 4, for ascertaining a measure of a calorific value of the gas G, the controllable voltage/current source 50 is connected to the first and second electrodes 30, 40 in order to apply the control voltage/control current between the first and second electrodes 30, 40. The control voltage/control current is generated with a level that is sufficient to pump oxygen from the reference gas environment U2 into the measuring gas G and to burn together with the combustible components of the gas G. The control voltage can have, for example, a level between 0.3 V and 2 V. The control apparatus 70 is designed to control the heating apparatus 20. The control apparatus 70 is designed, in particular, to actuate the heating apparatus 20 in successive heating periods in such a way that the heating apparatus 20 is deactivated during a first duration of each heating period and is activated during a second duration of each heating period, which follows the latter, to heat the diaphragm 10.

The heating apparatus 20 can be configured, for example, as a pulse-width-modulated heating apparatus that is deactivated during the first duration of each heating period and activated during the second duration of each heating period as a function of a PWM rate predefined by the control apparatus 70. The PWM rate, which therefore specifies the ratio between the switch-on and the switch-off times of the heating apparatus 20, is predefined by the control apparatus 70 as a function of the temperature of the diaphragm 10.

To ascertain the temperature of the diaphragm 10, a temperature-measuring apparatus 90 is provided. The temperature-measuring apparatus 90 can be coupled to the control apparatus 70. The control apparatus 70 is designed to set the ratio between the first and second duration, that is to say between the switch-on and switch-off durations of the heating apparatus as a function of the temperature of the diaphragm 10 ascertained by the temperature-measuring apparatus 90. If the temperature of the diaphragm 10 is, for example, below the threshold value temperature necessary for transporting the oxygen ions, the PWM rate or the ratio between the switch-on/switch-off times of the heating apparatus 20 is increased. On the other hand, if the temperature of the diaphragm 10 is significantly above the threshold value temperature necessary for transporting oxygen ions, the PWM rate or the ratio between the switch-on/switch-off times of the heating apparatus 20 is lowered. The evaluation apparatus 60 evaluates the ratio between the first and second durations of each heating period or the ratio between the switch-off/switch-on times of the heating apparatus 20 and acquires a measure of the calorific value of the gas G as a function of this ratio.

FIGS. 3 and 4 of the device for ascertaining a measure of the calorific value of a gas differ in that in FIG. 3 the diaphragm 10, the heating apparatus 20 and the first and second electrodes 30, 40 are embodied as part of a bistable probe, while in FIG. 4 the diaphragm 10, the heating apparatus 20 and the first and second electrodes 30, 40 are embodied as part of a linear lambda probe or broadband probe. In the embodiment 4, the pump cell 1220 can remain disconnected.

Figure 5:
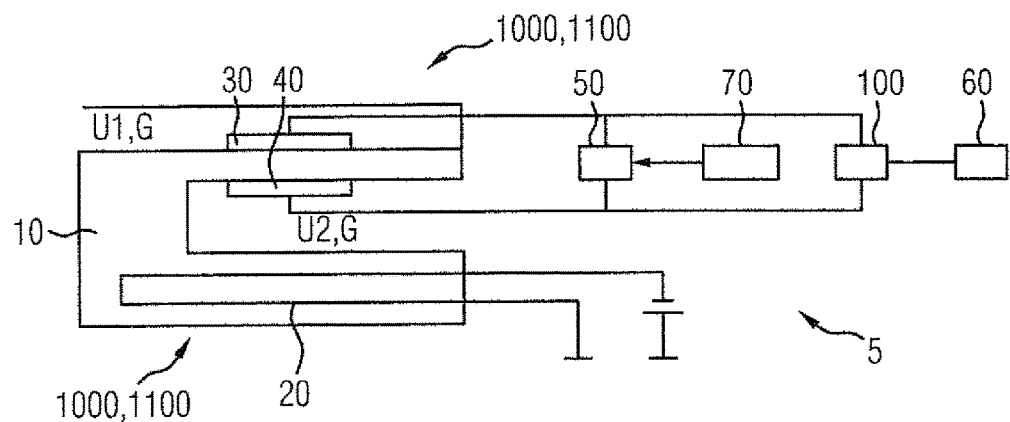
FIG. 5 is a device for ascertaining a measure of a calorific value of a gas.
Figure 6:
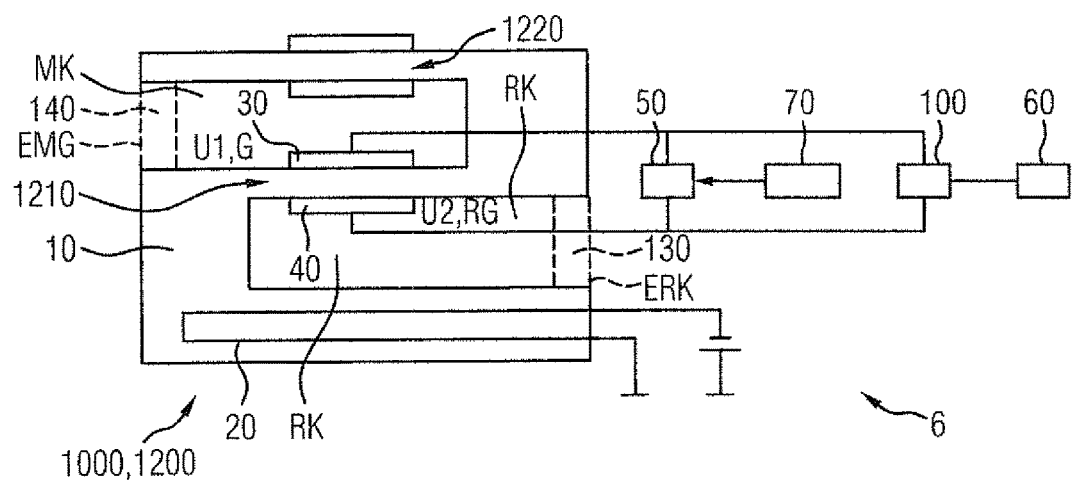
FIG. 6 is a device for ascertaining a measure of a calorific value of a gas.
Figure 7:
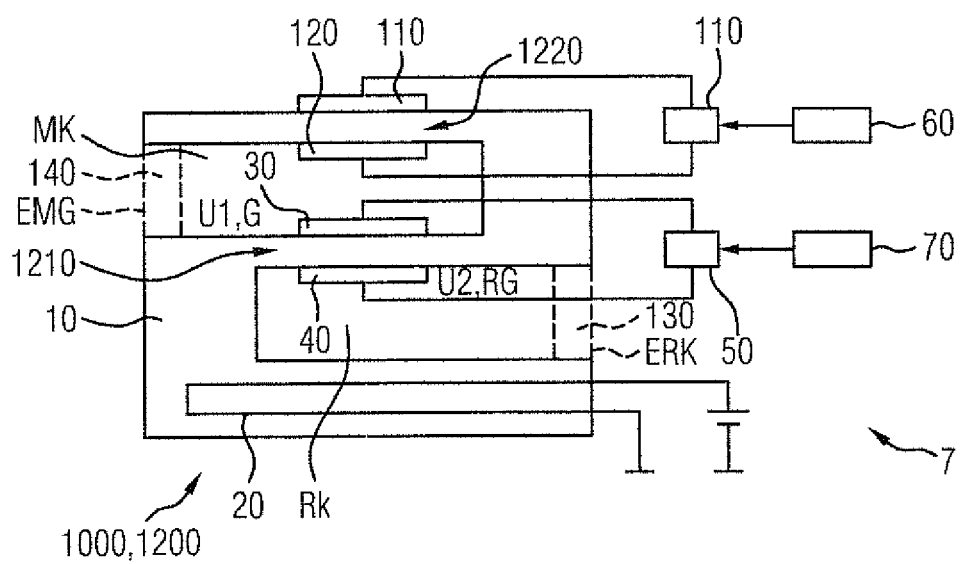
FIG. 7 is a device for ascertaining a measure of a calorific value of a gas.

In the devices shown in FIGS. 5, 6 and 7, for ascertaining a measure of a calorific value of the gas G, the controllable voltage/current source 50 is connected to the first and second electrodes 30, 40 to apply the control voltage/control current between the first and second electrodes 30, 40. The control voltage or the control current is generated with a level sufficient to pump oxygen from the reference gas environment U2 into the measuring gas G and to burn it together with the combustible components of the gas G.

The control voltage can be generated for this purpose, for example, with a level between 0.3 V and 2 V and can be applied to the first and second electrodes. The devices 5, 6 and 7 each have a measuring apparatus 100 for measuring the impedance of the diaphragm 10.

The evaluation apparatus 60 is designed to evaluate, during the first duration of each of the measuring time cycles, the impedance measured by the measuring apparatus 100 and to ascertain the measure of the calorific value of the gas G as a function of the evaluation. During this first duration, no control voltage/no control current is applied between the first and second electrodes. The application of the control voltage/control current for transporting oxygen into the gas G occurs during the second duration of each of the measuring time cycles, which follows the first duration. Conversely, during the second duration of each of the measuring time cycles, the measurement of the impedance of the diaphragm 10 is interrupted. Since the impedance of the diaphragm 10 is temperature-dependent, the temperature of the diaphragm 10 is also used in the devices as a measure of the calorific value of the gas G, owing to the exothermic reaction.

FIGS. 5, 6 and 7 of the device for ascertaining a measure of the calorific value of the gas G differ in that in FIG. 5 the diaphragm 10, the heating apparatus 20 and the first and second electrodes 30, 40 are embodied as part of a bistable probe, while in FIGS. 6 and 7 the diaphragm 10, the heating apparatus 20, and the first and second electrodes 30, 40 are embodied as part of a linear lambda probe or broadband probe. While in FIGS. 5 and 6, the measuring apparatus 100 for measuring the impedance of the diaphragm 10 is connected between the first and second electrodes, in FIG. 7 the device for ascertaining a measure of the calorific value of the gas G, the pump cell 1220 is used to determine the impedance of the diaphragm. In FIG. 7, the measuring apparatus 100 for measuring the impedance of the diaphragm is connected between the third electrode 110 and the fourth electrode 120, while in FIGS. 5 and 6 it is connected between the first and second electrodes 30, 40.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A device that ascertains a measure of a calorific value of a gas that has combustible components, comprising:
    a diaphragm having a first side and a second side that is different than the first side and configured to transport oxygen above a threshold value of a temperature;
    a heating apparatus configured to heat the diaphragm;
    a first electrode arranged on the first side of the diaphragm in a first environment that contains the gas;
    a second electrode arranged on the second side of the diaphragm in a second environment that contains a reference gas, which is different than the gas, with oxygen;
    one of a controllable voltage and a controllable current source for generating a respective control voltage or a control current between the first electrode and second electrode for controlling the transporting of the oxygen through the diaphragm; and an evaluation apparatus configured to ascertain the measure of the calorific value of the gas;
wherein the one of the controllable voltage and the controllable current source generates the respective control voltage or control current such that such a quantity of oxygen is transported through the diaphragm as a function of a level of the control voltage or the control current that the combustible components of the gas burn,
wherein the evaluation apparatus ascertains the measure of the calorific value of the gas as a function of one of a level of a temperature of the diaphragm and an impedance of the diaphragm.

2. The device as claimed in claim 1, further comprising:
a control apparatus configured to control the one of the controllable voltage source and the controllable current source,
wherein the control apparatus controls the one of the controllable voltage source and the controllable current source in successive time cycles such that during a first duration of each of the time cycles the respective control voltage or control current is not generated, and during a second duration of each of the time cycles, which follows the first duration, the respective control voltage or control current is generated with the level.

3. The device as claimed in claim 2, comprising:
a voltage measuring apparatus configured to ascertain a voltage level between the first electrode and the second electrode during the first duration of each of the time cycles,
wherein the control apparatus actuates the one of the controllable voltage source and the controllable current source such that the one of the controllable voltage source and the controllable current source generates the level of the respective control voltage or control current during the second duration of each of the time cycles as a function of the voltage level ascertained during the first duration.

4. The device as claimed in claim 2, wherein:
the control apparatus controls the heating apparatus,
the control apparatus actuates the heating apparatus in successive heating periods such that the heating apparatus is deactivated during a first duration of each heating period and activated during a second duration of each heating period that follows the first duration to heat the diaphragm.

5. The device as claimed in claim 4, further comprising:
a temperature measuring apparatus for ascertaining a temperature of the diaphragm,
wherein the control apparatus is designed to set a ratio of the first duration and the second duration of each heating period as a function of the temperature of the diaphragm ascertained by the temperature measuring apparatus.

6. The device as claimed in claim 5,
wherein the evaluation apparatus evaluates the ratio of the first duration and second duration of each heating period and ascertains the measure of the calorific value of the gas as a function of the ratio.

7. The device as claimed in claim 2, further comprising:
a measuring apparatus configured to measure the impedance of the diaphragm,
wherein the evaluation apparatus evaluates, during the first duration of each of the time cycles, the impedance measured by the measuring apparatus and ascertains the measure of the calorific value of the gas as a function of the evaluation.

8. The device as claimed in claim 1, comprising:
a lambda probe that contains the diaphragm, the heating apparatus, and the first electrode and second electrode.

9. The device as claimed in claim 8,
wherein the lambda probe is one of a bistable probe and a broadband probe.

10. The device as claimed in claim 8,
wherein the lambda probe is a broadband probe that comprises a Nernst cell and a pump cell having a third electrode and a fourth electrode,
wherein the Nernst cell comprises the diaphragm, the first electrode, and the second electrode,
wherein a measuring apparatus for measuring the impedance of the diaphragm is arranged between the third electrode and the fourth electrode.

11. The device as claimed in claim 8,
wherein the lambda probe comprises a channel with an inlet opening that feeds the reference gas into the channel,
wherein the second electrode is arranged in the channel, and
wherein a diffusion barrier that inputs the reference gas into the channel is arranged at the inlet opening (ERK) of the channel.

12. A method for ascertaining a measure of a calorific value of a gas that has combustible portions, comprising:
providing a device for ascertaining a calorific value of a gas having a diaphragm having a diaphragm having a first side and a second side that is different than the first side and configured to transport oxygen above a threshold value of a temperature, a heating apparatus configured to heat the diaphragm, a first electrode arranged on the first side of the diaphragm in a first environment that contains the gas; a second electrode arranged on the second side of the diaphragm in a second environment that contains a reference gas, which is different than the gas, with oxygen, one of a controllable voltage and a controllable current source for generating a respective control voltage or a control current between the first electrode and second electrode for controlling the transporting of the oxygen through the diaphragm, and an evaluation apparatus;
arranging the device such that the first electrode is arranged in the first environment and the second electrode is arranged in the second environment;
applying the respective control voltage or the control current between the first electrode and the second electrode with a level such that a quantity of oxygen is transported from the second environment through the diaphragm to the first environment such that the combustible portions of the gas burn;
burning the oxygen in the first environment of the first electrode;
acquiring the measure of the calorific value of the gas by evaluating one of a level of the temperature of the diaphragm or an impedance of the diaphragm during combustion.

13. The method as claimed in claim 12, further comprising:
measuring a level of the voltage between the first electrode and the second electrode;
regulating the level of the respective control voltage or the control current as a function of the measured voltage level,
wherein the measurement of the voltage level between the first electrode and the second electrode and the regulating of the control voltage or the control current in successive time cycles occurs such that during a first duration of each of the time cycles no respective control voltage or respective control current is applied between the first electrode and the second electrode and the voltage level between the first electrode and the second electrode is measured, and during a second time period of each of the time cycles, which follows the first time period, the control voltage or the control current is generated as a function of the voltage level measured between the first electrode and the second electrode.

14. The method as claimed in claim 12, comprising:

deactivating and activating the heating apparatus in successive heating periods such that the heating apparatus is deactivated during a first duration of each heating period and is activated during a second duration that follows the first duration of each heating period to heat the diaphragm, setting a ratio between the first duration and the second durations of each heating period as a function of the acquired level of the temperature of the diaphragm, acquiring the measure of the calorific value of the gas as a function of the set ratio between the first and duration and the second durations of each heating period.

15. The method as claimed in claim 12, comprising:

deactivating and activating generation of the control voltage or the control current in successive time cycles such that during a first duration of each of the time cycles the control voltage or the control current is not applied between the first electrode and the second electrode, and the impedance of the diaphragm is measured, and during a second duration of each of the time cycles, which follows the first duration, the control voltage or the control current is generated between the first electrode and the second electrode, and the measurement of the impedance of the diaphragm is interrupted.

* * * * *